(12) United States Patent
Sugiyama et al.

(10) Patent No.: US 9,044,624 B2
(45) Date of Patent: Jun. 2, 2015

(54) SUNSCREEN COMPOSITION

(75) Inventors: Yuki Sugiyama, Kanagawa (JP); Koji Abe, Kanagawa (JP); Susumu Yoshida, Kanagawa (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 13/581,601

(22) PCT Filed: Mar. 2, 2011

(86) PCT No.: PCT/JP2011/054755
§ 371 (c)(1),
(2), (4) Date: Aug. 28, 2012

(87) PCT Pub. No.: WO2011/108583
PCT Pub. Date: Sep. 9, 2011

(65) Prior Publication Data
US 2012/0321576 A1 Dec. 20, 2012

(30) Foreign Application Priority Data
Mar. 4, 2010 (JP) ................................. 2010-047572

(51) Int. Cl.
| A61K 8/92 | (2006.01) |
| A61Q 17/04 | (2006.01) |
| A61K 8/06 | (2006.01) |
| A61K 8/37 | (2006.01) |
| A61K 8/39 | (2006.01) |

(52) U.S. Cl.
CPC ............... *A61Q 17/04* (2013.01); *A61K 8/068* (2013.01); *A61K 8/37* (2013.01); *A61K 8/39* (2013.01); *A61K 2800/596* (2013.01)

(58) Field of Classification Search
None
See application file for complete search history.

(56) References Cited

U.S. PATENT DOCUMENTS

| 6,528,070 | B1 * | 3/2003 | Bratescu et al. ............... 424/401 |
| 6,710,038 | B1 * | 3/2004 | Hirai et al. ....................... 514/54 |
| 2006/0057168 | A1 * | 3/2006 | Larm et al. ...................... 424/400 |
| 2006/0078525 | A1 * | 4/2006 | Tomokuni .................. 424/70.13 |
| 2007/0060495 | A1 * | 3/2007 | Mock-Knoblauch et al. ............................. 510/475 |
| 2007/0141090 | A1 * | 6/2007 | Harris et al. ................... 424/400 |
| 2008/0293603 | A1 * | 11/2008 | Watanabe et al. ............. 510/136 |
| 2013/0164246 | A1 * | 6/2013 | Kurashima et al. ........ 424/70.13 |

FOREIGN PATENT DOCUMENTS

| JP | 1-155941 | 6/1989 |
| JP | 1-288330 | 11/1989 |
| JP | 9-175975 | 7/1997 |
| JP | 9-175978 | 7/1997 |
| JP | 2001-501635 | 2/2001 |
| JP | 2004-217640 | 8/2004 |
| JP | 2005-538135 | 12/2005 |
| JP | 2007-518757 | 7/2007 |
| JP | 2008-517051 | 5/2008 |
| JP | 2008-184413 | 8/2008 |
| WO | WO2007135196 | * 11/2007 ............... A61K 8/92 |

OTHER PUBLICATIONS

Tyagi et al. Fatty imidazoline: chemistry, synthesis, properties and their industrial application, J. Oleo. Sci., 2007, vol. 55, pp. 319-329.*
Lawrence et al., Noninoic oil-in-water microemulsions: the effect of oil type on the phase behaviour, Int. J. Pharm., 2000, vol. 198, pp. 7-27.*
Skoviera et al., Microemulsions as vehicles for transdermal permeation of drugs, Acta Facultatis Pharmaceuticae Universitatis Comenianae, 2003, p. 147-155.*
Pluronic and Tetronic catalog page.*
Garti, formation and characterization of odered bicontinuous microemulsions, J. phys. chem., 2009, vol. 113, pp. 10669-10678.*
Oetter, et al., Ringing gels: their structure and macroscopic properties, Colloid Polym. Sci., 1990, vol. 266, pp. 167-178.*
Masuda et al. In Microemulsion formulation for enhanced absorption of poorly water soluble drugs, I. Prescription design, Journal of Controlled Release, 2002, vol. 81, pp. 65-74.*
PCT/JP2011/054755, International Preliminary Report and Written Opinion, mailed Oct. 11, 2012, 6 pages—English.
PCT/JP2011/054755 ISR mailed Jun. 14, 2011, English 4 pges, Japanese 5 pges-.
PCT/JP2011/054755 Written Opinion mailed Jun. 1, 2011, English 3 pgs., Japanese 4 pages.
JPO Reasons for Refusal for JP2010-047572, dated Jun. 10, 2011, English (3pgs), Japanese (3pgs).
JPO Decisions to Grant for JP2010-047572, dated Sep. 9, 2011, English (4pgs), Japanese (3pgs).
Granted Claims of JP-B2-4834775, English (4pgs), Japanese (4 pgs).
Kei Watanabe, "Innovation in the Key performance of the cleansing oil by controlling the phas sequence of the surfactant system", Fragrance Journal, vol. 35, No. 4, Apr. 15, 2007, pp. 65-70.
Takeaki Nagamatsu, "1, 2-Alkanedoil no D-so Gel ni Oyobosu Eikyo", Fragramce Journal, Dec. 15, 2007, vol. 35, No. 12, p. 73.
Hiroko Tsuda, "Development Trend of Makeup and Pore Cleansing Technology", Fragrance Journal, Dec. 15, 2008, vol. 36, No. 12, pp. 24-29.
Michihiro Yamaguchi, "Evidence ni Motozuku Yuyosei no Tsuikyo to Keshohin no Saranaru Shinka ni Mukete", Fragrance Journal, May 15, 2003, vol. 31, No. 5, pp. 22-25.

* cited by examiner

*Primary Examiner* — Kevin S Orwig
*Assistant Examiner* — Ping Cao
(74) *Attorney, Agent, or Firm* — Andrew F. Young, Esq.; Lackenbach Siegel, LLP

(57) ABSTRACT

The present invention provides a sunscreen composition containing (a) a surfactant, (b) water, (c) an oil component, and (d) a water- and/or oil-soluble ultraviolet absorbent, that is in a bicontinuous microemulsion phase at 25° C. The transparent bicontinuous microemulsion spreads well when applied to the skin, to give a uniform and well-absorbed film.

4 Claims, 4 Drawing Sheets

SUNSCREEN COMPOSITION

TECHNICAL FIELD

The present invention relates to a sunscreen composition used as a sunscreen cosmetic. More specifically, it relates to a sunscreen composition composed of a transparent bicontinuous microemulsion phase that is superior in ultraviolet protection and stability, spreads well on the skin at the time of application, exhibits superior coating film uniformity, and is absorbed well.

BACKGROUND ART

Usually, ultraviolet absorbents and/or ultraviolet scattering agents (zinc oxide, titanium oxide, etc.) are added to sunscreen cosmetics in order to block ultraviolet irradiation to the skin to achieve a high SPF (Sun Protection Factor) (refer to Patent Documents 1-3, for example). Examples of types of such sunscreen compositions include the oil-in-water emulsified type and the water-in-oil emulsified type.

The oil-in-water type as shown in Patent Documents 1-2 is preferably used to obtain refreshing and dewy, fresh texture. However, oil-in-water emulsified compositions cannot contain a large quantity of the oil component, which is to be the inner phase, due to the stability issue of the emulsified system.

Also, since stickiness arises when a large quantity of the oil component is blended in, it is not a common practice to blend in a large quantity of the oil component because the texture is of particular importance in cosmetics. Therefore, it is difficult to blend a large quantity of an oil soluble ultraviolet absorbent into an oil-in-water emulsified compositions while maintaining the characteristic refreshing, dewy, fresh and water like texture; as a result, it cannot have a high ultraviolet protection ability compared with other emulsified type sunscreen compositions.

Therefore, sometimes a water soluble ultraviolet absorbent, in addition to said oil soluble ultraviolet absorbent, is added so that the blend ratio of the oil soluble stays low and therefore a high ultraviolet protection ability is obtained while the dewy, fresh texture characteristic to oil-in-water emulsified compositions is maintained (see Patent Document 4, for example). However, when a water soluble ultraviolet absorbent is blended in, salt (neutralization salt) is usually blended in to maintain the system stability. This elevates the salt concentration in the emulsified composition and cancels out the electrostatic repulsion between the emulsified particles, which in some cases drastically worsens the emulsification stability.

In a water-in-oil emulsified sunscreen composition (see Patent Document 5, for example), the oil phase is the continuous phase (outer phase). Therefore, compared with oil-in-water sunscreen compositions, a larger quantity of the oil component and/or the oil soluble ultraviolet absorbent can be blended in to obtain a high ultraviolet protection ability. When it is used it leaves on the skin surface an oil film with a low moisture permeability that protects the skin from drying for a long time; furthermore, it doesn't re-emulsify easily when exposed to water in situations including bathing, washing/cleaning, and perspiration; for these reasons, it is used as an antiperspirant/water resistant base agent in sunscreen compositions.

However, a conventional water-in-oil emulsified sunscreen composition must dissolve a large quantity of a highly polar ultraviolet absorbent in the oil phase, resulting in separation and aggregation over a period of time; hence there is the problem of poor long term stability.

Also, in terms of texture as an external preparation, compared with an oil-in-water type sunscreen cosmetic, it has problems such as stickiness, oiliness, and poor spreadability.

On the other hand, whereas an emulsified composition is the non-equilibrium system, in which water is dispersed in oil, or oil is dispersed in water, as emulsified particles, microemulsion is an equilibrium isotropic low viscosity solution, in which water is solubilized in oil or oil is solubilized in water. There are three types of microemulsion, i.e. the micelle aqueous solution phase, in which oil is solubilized in water, the reverse micelle oil solution, in which water is solubilized in oil, and the bicontinuous microemulsion.

In the micelle aqueous solution phase, water forms a continuous state and sphere-like or rod-like aggregates, with the lipophilic groups of the surfactant facing inward, are dispersed. The size of the aggregate is up to about 100 nm; the external appearance is optically isotropic and transparent or bluish semi-transparent. When a micro aqueous solution is used as a sunscreen composition, it is generally not possible to solubilize a large quantity of oil components and therefore the blend ratio of the oil soluble ultraviolet absorbent cannot be raised, which makes it impossible to obtain a high ultraviolet protection ability.

The reverse micelle oil solution phase is a dispersion of spherical or rod-like aggregates having the hydrophilic groups of the surfactant facing inward. When a micro oil solution phase is used as a sunscreen composition, it is not possible to solubilize a large quantity of water and therefore stickiness and the oily sensation are pronounced, which makes it impossible to obtain a satisfactory texture during use.

On the other hand, the bicontinuous microemulsion phase is generally formed under conditions where hydrophilicity and hydrophobicity are in balance; because the interfacial tension becomes the minimum, the number of surfactant aggregates increases and form aggregates infinitely, and as a result the soluble quantity of water and oil drastically increases and thus a solubilized system having a specific structure of continuous channels of water and oil is formed.

It is said that searching for a combination of chemical compounds that meets the formation condition of a bicontinuous microemulsion phase is very difficult and the range of formation conditions is very narrow. Therefore, although it is often observed as a three phase state of oil phase/bicontinuous microemulsion phase/water phase in which it coexists with non-solubilized excess water or oil (Non-Patent Document 1, for example), there are not many reports of the bicontinuous microemulsion phase observed as one state. For example, it has been reported that the bicontinuous microemulsion phase can be obtained by either using polyoxyethylene lauryl ether (4EO) for the surfactant and isohexadecane for the oil component (Non-Patent Document 2), or using a didecyl methyl ammonium salt for the surfactant and dodecane for the oil component (Non-Patent Document 3), or using soy phospholipid for the surfactant, propanol for the detergency builder, and triglyceride for the oil component (Non-Patent Document 4).

Also, it has been reported that a bicontinuous microemulsion phase can be obtained by either using polyethylene glycol monolaurate (12EO) for the surfactant, lauryl alcohol and ethanol for the detergency builder, and liquid isoparaffin for the oil component (Patent Document 6), or using POE (8) glyceryl isostearate for the surfactant and cetyl octanoate liquid paraffin for the oil component (Patent Document 7), or using imidazolium betaine and POE lauryl ether sulfate for the surfactant, and a mono glycerol mono fatty acid ester and/or monoalkyl mono glyceryl ether for the oil component (Patent Document 8).

The bicontinuous microemulsion phase assumes a unique structure in which both water and oil are continuous and therefore, compared with the micelle phase, it can contain more oil components and/or or oil-based ingredients. Also, compared with the reverse micelle phase, it can contain more water and water-based ingredient. There are many reports of it as a cleaning agent that is highly capable of cleaning both oil-based stains and water soluble stains and rinses well (for example, see Patent Documents 6-10) wherein its ability to mix well with both water and oil and its low interfacial tension were utilized. However, currently, industrial utilization outside of cleaning purposes is marginal; no utilization is known for sunscreen compositions such as sunscreen cosmetics.

PRIOR ART DOCUMENTS

Patent Documents

Patent Document 1: JP 2002-284638 A
Patent Document 2: JP 2005-255669 A
Patent Document 3: JP H5-97644 A
Patent Document 4: JP 2008-162930 A
Patent Document 5: JP H9-255544 A
Patent Document 6: JP 2004-217640 A
Patent Document 7: JP 2005-194249 A
Patent Document 8: JP 2007-77302 A
Patent Document 9: Japanese Patent No. 3684144 bulletin
Patent Document 10: JP 2009-196909 A Non-Patent Documents Non-Patent Document 1: Langmuir, 1997, 13, 2001-2006.
Non-Patent Document 2: Langmuir, 2004, 20, 6594-6598.
Non-Patent Document 3 Langmuir, 2003, 19, 7196-7200.
Non-Patent Document 4: Langmuir, 1997, 13, 5061-5070.

DISCLOSURE OF INVENTION

Technical Problem

The object of the present invention is to utilize a bicontinuous microemulsion phase to provide a sunscreen composition that is superior in terms of the ultraviolet protection and stability, as well as the tactile sensation during use.

Technical Solution

The present invention provides a sunscreen composition comprising (a) a surfactant, (b) water, (c) an oil component, and (d) a water soluble ultraviolet absorbent and/or oil soluble ultraviolet absorbent that is in the bicontinuous microemulsion phase at 25° C.

Also, the present invention provides the aforementioned sunscreen composition wherein said ingredient (a) a surfactant is an ionic and/or nonionic surfactant.

Furthermore, the present invention provides the aforementioned sunscreen composition wherein said ingredient (a) surfactant is selected from a combination of an anionic surfactant and an ampholytic surfactant and a combination of an anionic surfactant and a cationic surfactant.

Also, the present invention provides the aforementioned sunscreen composition wherein said ingredient (a) a surfactant is a nonionic surfactant whose HLB is between 5 and 14.

Furthermore, the present invention provides the aforementioned sunscreen composition wherein said ingredient (d) water soluble ultraviolet absorbent is one, two, or more selected from phenylbenzimidazole sulfonate, 2-hydroxy-4-methoxy benzophenone-5-sulfonate, 4-(2-β-glucopyrano-siloxy)propoxy-2-hydroxybenzophenone, and bis-sodium phenylene-1,4-bis(2-benzimidazyl)-3,3'-5,5'-tetrasulfonate.

Furthermore, the present invention provides the aforementioned sunscreen composition wherein said ingredient (d) oil soluble ultraviolet absorbent is one, two, or more selected from 2-ethylhexyl-p-methoxycinnamate, 4-tert-4'-methoxy-dibenzoylmethane, octocrylene, 2,4-bis-[{4-(2-ethylhexyloxy)-2-hydroxy}-phenyl]-6-(4-methoxyphenyl)-1,3,5-triazine, methylene bis benzotriazolyl tetramethylbutylphenol, 2,4,6-tris-[4-(2-ethylhexyloxycarbonyl)anilino]1,3,5-triazine, diethylamino hydroxybenzoyl hexyl benzoate, oxybenzone, and dihydroxy dimethoxy benzophenone.

Advantageous Effects of the Invention

The present invention make it possible, by using the bicontinuous microemulsion phase, to obtain a sunscreen composition that manifests excellent ultraviolet protection and a superior texture during use. Furthermore, it can provide a sunscreen cosmetic composed of a sunscreen composition that uses a transparent bicontinuous microemulsion phase that spreads well on the skin at the time of application, exhibits superior coating film uniformity, and is absorbed well.

BEST MODE FOR CARRYING OUT THE INVENTION

Figure 1:
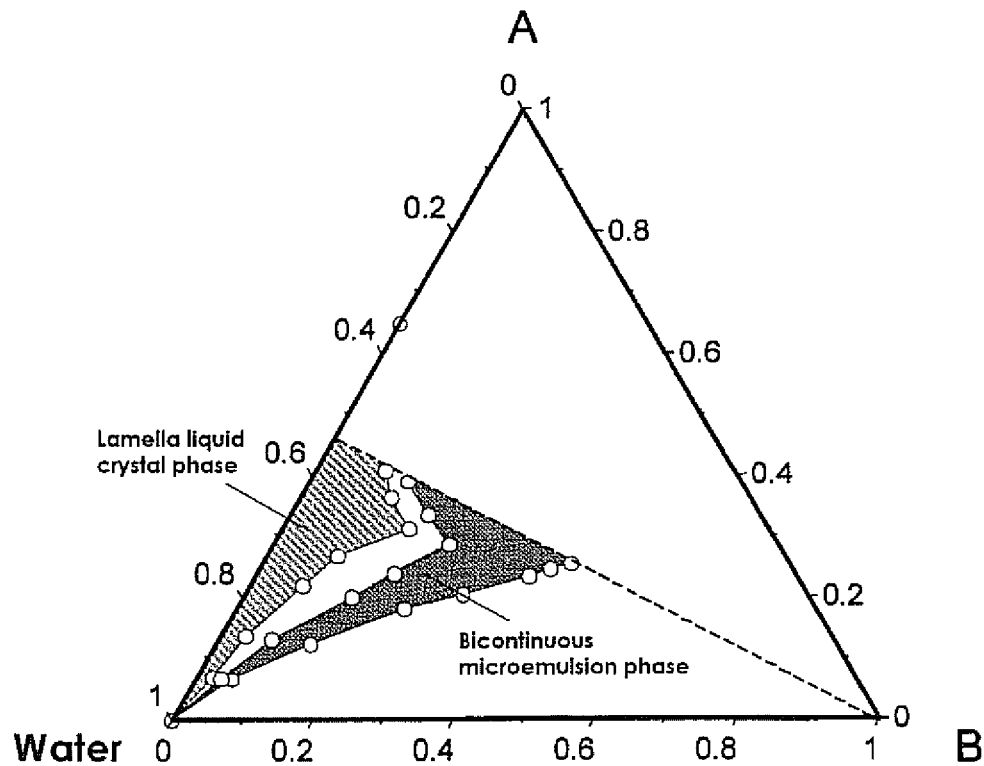
FIG. 1 is a phase diagram for determining the blend ratios of the essential ingredients (a)-(d) to prepare a sunscreen composition in the bicontinuous microemulsion phase.

The preferred embodiments of the present invention are described in detail below.

<(a) Surfactant>

(a) the surfactant used in the present invention is an ionic and/or nonionic surfactant.

An ionic surfactant is a surfactant that is ionized to have an electric charge in an aqueous solution; depending on the type of the electric charge, it is classified into ampholytic surfactants, cationic surfactants, or anionic surfactants.

An ampholytic surfactant has at least one cationic functional group and one anionic functional group, is cationic when the solution is acidic and anionic when the solution is alkaline, and assumes characteristics similar to a nonionic surfactant around the isoelectric point.

Ampholytic surfactants are classified, based on the type of the anionic group, into the carboxylic acid type, the sulfuric ester type, the sulfonic acid type, and the phosphoric ester type. For the present invention, the carboxylic acid type, the sulfuric ester type, and the sulfonic acid type are preferable. The carboxylic acid type is further classified into the amino acid type and the betaine type. Particularly preferable is the betaine type.

Specific examples include: imidazoline type ampholytic surfactants (for example, 2-undecyl-1-hydroxyethyl-1-carboxymethyl-4,5-dihydro-2-imidazolium sodium salt and 1-[2-(carboxymethoxy)ethyl]-1-(carboxymethyl)-4,5-dihydro-2-norcocoalkylimidazolium hydroxide disodium salt); and betaine type surfactants (for example, 2-heptadecyl-N-carboxymethyl-N-hydroxyethyl imidazolinium betaine, lauryldimethylarninoacetic acid betaine, alkyl betaine, amide betaine, and sulfobetaine).

Examples of the cationic surfactant include quaternary ammonium salts such as cetyltrimethylammonium chloride, stearyltrimethylammonium chloride, benenyltrimethylammonium chloride, behenyldimethylhydroxyethylammonium chloride, stearyldimethylbenzylammonium chloride, and cetyltrimethylammonium methylsulfate. Other examples include amide amine compounds such as stearic diethylaminoethylamide, stearic dimethylaminoethylamide, palmitic diethylaminoethylamide, palmitic dimethylaminoethylamide, myristic diethylaminoethylamide, myristic dimethylaminoethylamide, behenic diethylaminoethylamide, behenic dimethylaminoethylamide, stearic diethylaminopropylamide, stearic dimethylaminopropylamide, palmitic diethylaminopropylamide, palmitic dimethylaminopropylamide, myristic diethylaminopropylamide, myristic dimethylaminopropylamide, behenic diethylaminopropylamide, and behenic dimethylaminopropylamide.

Anionic surfactants are classified into the carboxylate type such as fatty acid soaps, N-acyl glutamates, and alkyl ether acetates, the sulfonic acid type such as α-olefin sulfonates, alkane sulfonates, and alkylbenzene sulfonates, the sulfuric ester type such as higher alcohol sulfuric ester salts, and phosphoric ester salts. Preferable are the carboxylate type, the sulfonic acid type, and the sulfuric ester salt type; particularly preferable is the sulfuric ester salt type.

Specific examples include fatty acid soaps (for example, sodium laurate and sodium palmitate); higher alkyl sulfuric acid ester salts (for example, sodium lauryl sulfate and potassium lauryl sulfate); alkyl ether sulfuric acid ester salts (for example, POE-triethanolamine lauryl sulfate and sodium POE-lauryl sulfate); N-acyl sarcosinic acids (for example, sodium lauroyl sarcosinate); higher fatty acid amide sulfonic acid salts (for example, sodium N-myristoyl N-methyl taurate, Sodium N-cocoyl-N-methyl taurate, and Sodium jauroylmethyl taurate); phosphoric ester salts (for example, sodium POE-oleyl ether phosphate and POE stearyl ether phosphoric acid); sulfosuccinates (for example sodium di-2-ethylhexylsulfosuccinate, sodium monolauroyl monoethanol amide polyoxyethylene sulfosuccinate, and sodium lauryl polypropylene glycol sulfosuccinate); alkyl benzene sulfonates (for example, sodium linear dodecyl benzene sulfonate, triethanolamine linear dodecyl benzene sulfonate, and linear dodecyl benzene sulfonic acid); higher fatty acid ester sulfates (for example, hydrogenated coconut oil aliphatic acid glyceryl sodium sulfate); N-acyl glutamates (for example, mono sodium N-lauroylglutamate, disodium N-stearoylglutamate, and sodium N-myristoyl-L-glutamate); sulfated oils (for example, turkey red oil); POE-alkyl ether carboxylic acid; POE-alkyl aryl ether carboxylate; α-olefin sulfonate; higher fatty acid ester sulfonates; sec-alcohol sulfates; higher fatty acid alkyl amide sulfates; sodium lauroyl monoethanolamine succinates; ditriethanolamine N-palmitoylaspartate; and sodium caseinate.

When an anionic surfactant and an ampholytic surfactant, or an anionic surfactant and a cationic surfactant, are mixed in an aqueous solution, it is known that the interfacial tension against oil decreases. Therefore, a bicontinuous microemulsion, in which the oil-water interfacial tension is the minimum, can be easily generated, making such combinations preferable for the present invention.

When only one of an ampholytic surfactant, cationic surfactant, or anionic surfactant is used, the reduction in the interfacial tension is not sufficient and therefore the bicontinuous microemulsion phase cannot be obtained or, even if it can be obtained, it can only be generated in a narrow region and stability may not be satisfied sufficiently for practical use.

A nonionic surfactant is a surfactant that is not ionized and assumes an electric charge in an aqueous solution. For the hydrophobic group, a type that uses alkyls and a type that uses dimethyl silicone are known among others. Specific examples of the former include glycerol fatty acid esters, ethylene oxide derivatives of glyceryl fatty acid esters, polyglycerol fatty acid esters, propylene glycol fatty acid esters, ethylene oxide derivatives of propylene glycol fatty acid esters, polyethylene glycol fatty acid esters, polyethylene glycol alkyl ethers, polyethylene glycol alkyl phenyl ethers, polyethylene glycol castor oil derivatives, and polyethylene glycol hydrogenated castor oil derivatives. Examples of the latter include polyether-modified silicone and polyglycerin-modified silicone. Preferable is the type that uses alkyl for the hydrophobic group.

Specific examples of the lipophilic nonionic surfactants include sorbitan fatty acid esters (for example, sorbitan mono oleate monooleate, sorbitan mono isostearate monoisostearate, sorbitan mono laurate monolaurate, sorbitan mono palmitate monopalmitate, sorbitan mono stearate monostearate, sorbitan sesquioleate, sorbitan trioleate, diglyceryl sorbitan penta-2-ethylhexylate, diglyceryl sorbitan tetra-2-ethylhexylate); glyceryl and polyglyceryl aliphatic acids (for example, mono cottonseed oil fatty acid glycerine, glyceryl monoerucate, glyceryl sesquioleate, glyceryl monostearate, α,α'-glyceryl oleate pyroglutamate, monostearate glyceryl malic acid); propylene glycol fatty acid esters (for example, propylene glycol monostearate); hydrogenated castor oil derivatives; and glyceryl alkylethers.

Examples of hydrophilic nonionic surfactants include POE-sorbitan fatty acid esters (for example, POE-sorbitan monooleate, POE-sorbitan monostearate, POE-sorbitan monooleate, and POE-sorbitan tetraoleate); POE sorbitol fatty acid esters (for example, POE sorbitol monolaurate, POE-sorbitol monooleate, POE-sorbitolpentaoleate, and POE-sorbitol monostearate); POE-glyceryl fatty acid esters (for example, POE-monooleates such as POE-glyceryl monostearate, POE-glyceryl monoisostearate, and POE glyc- erin glyceryl triisostearate); POE-fatty acid esters (for example, POE-distearate, POE-monodioleate, and ethylene glycol distearate); POE-alkylethers (for example, POE-lauryl ether, POE-oleyl ether, POE-stearyl ether, POE-behenyl ether, POE 2-octyl dodecyl ether, and POE-cholestanol ether); pluaronics (for example, pluaronic); POE•POP-alkylethers (for example, POE•POP-cetyl ether, POE•POP2-decyl tetradecyl ether, POE•POP-monobutyl ether, POE•POP-lanolin hydrate, and POE•POP glycerin glyceryl ether); tetra POE•tetra POP-ethylenediamino condensates (for example, tetronic); POE-castor oil hydrogenated castor oil derivatives (for example, POE-castor oil, POE-hydrogenated castor oil, POE-hydrogenated castor oil monoisostearate, POE-hydrogenated castor oil triisostearate, POE-hydrogenated castor oil monopyroglutamic monoisostearic diester, and POE-hydrogenated castor oil maleic acid); POE-beeswax•lanolin derivatives (for example, POE-sorbitol beeswax); alkanol amides (for example, palm oil fatty acid diethanol amide, laurate monoethanolamide, and fatty acid isopropanol amide); POE-propylene glycol fatty acid esters; POE-alkylamines; POE-fatty acid amides; sucrose fatty acid esters; alkyl ethoxydimethylamine oxides; and trioleyl phosphoric acid.

In the present invention, the nonionic surfactant should preferably have an HLB of 5-14. It is generally known that the solubility into water and the solubility into oil balance when the HLB is 7. That is, a surfactant preferable for the present invention would have medium solubility in oil/water. If the HLB is less than 5 or more than 14, then the bicontinuous microemulsion phase cannot be obtained or, even if it can be obtained, it can only be generated in a narrow region and stability may not be satisfactory for practical use.

Also, an ingredient called a "cosurfactant", which functions as a surfactant builder, can be blended into the present invention. Examples include mono-glycerol derivatives and/or diglycerol derivatives. Specific examples include: monoglycerol derivatives such as monoglycerol monooctanoate, monooctyl monoglyceryl ether, monoglycerol monononanoate, monononyl monoglyceryl ether, monoglycerol monodecanoate, monodecyl monoglyceryl ether, monoglycerol monoundecylenate, monoundecylenyl glyceryl ether, monoglycerol monododecanoate, monododecyl monoglyceryl ether, monoglycerol monotetradecanoate, monoglycerol monohexadecanoate, monoglycerol monooleate, and monoglycerol monoisostearate, as well as diglycerol derivatives such as diglycerol monooctanoate, monooctyl diglyceryl ether, diglycerol monononanoate, monononyl diglyceryl ether, diglycerol monodecanoate, monodecyl diglyceryl ether, diglycerol monoundecylenate, monoundecylenyl glyceryl ether, diglycerol monododecanoate, monododecyl diglyceryl ether, diglycerol monotetradecanoate, diglycerol monohexadecanoate, diglycerol monooleate, and diglycerol monoisostearate.

<Blend Ratio>

The blend ratio of the surfactant is appropriately determined based on the phase diagram; it is preferably 0.1-50 wt %, more preferably 0.3-30 wt % relative to the total amount of the sunscreen composition.

<(b) Water>

Selection of the water contained in the sunscreen composition of the present invention is not limited in particular; specific examples include purified water, ion-exchanged water, and tap water.

<Blend Ratio>

The blend ratio of water is determined appropriately based on the phase diagram; it is preferably 1-95 wt % relative to the total amount of the sunscreen composition.

<(c) Oil Component>

Examples of the oil component used in the sunscreen composition of the present invention include hydrocarbon oils, higher fatty acids, higher alcohols, synthetic esters, silicone oils, liquid fats and oils, solid fats and oils, and waxes that are commonly used in cosmetics, quasi-drugs, etc.; one, two, or more oil components can be used.

Examples of the hydrocarbon oils include liquid petrolatum, ozocerite, squalane, pristane, paraffin, ceresin, squalene, petrolatum, and microcrystalline wax.

Examples of the higher fatty acids include lauric acid, myristic acid, palmitic acid, stearic acid, behenic acid, oleic acid, undecylenic acid, tall oil, isostearic acid, linolic acid, linoleic acid, eicosapentaenoic acid (EPA), and docosahexaenoic acid (DHA).

Examples of the higher alcohols include straight chain alcohols (for example, lauryl alcohol, cetyl alcohol, stearyl alcohol, behenyl alcohol, myristyl alcohol, oleyl alcohol, and cetostearyl alcohol) and branched chain ethyl alcohols (for example, mono stearyl glyceryl ether (batyl alcohol), 2-decyltetradecynol, lanolin alcohol, cholesterol, phytosterol, hexyl dodecanol, isostearyl alcohol, and octyl dodecanol).

Examples of the synthetic ester oils include octyl octanoate, nonyl nonanoate, cetyl octanoate, isopropyl myristate, octyl dodecyl myristate, isopropyl palmitate, butyl stearate, hexyl laurate, myristyl myristate, decyl oleate, dimethyl hexyl decyl octanoate, cetyl lactate, myristyl lactate, lanolin acetate, isocetyl stearate, isocetyl isostearate, cholesteryl 12-hydroxystearate, di-2-ethylene glycol ethylhexanoate, dipentaerythritol fatty acid ester, N-alkylene glycol monoisostearate, neopentyl glycol dicaprate, tripropylene glycol pivalate, diisostearyl malate, glyceryl di-2-heptylundecanoate, glyceryl diisostearate, trimethylolpropane tri-2-ethyl hexanoate, trimethylolpropane triisostearate, tetra-2-pentaerythritol ethylhexanoate, glyceryl tri-2-ethylhexanoate, glyceryl trioctanoate, glyceryl triisopalmitate, trimethylolpropane triisostearate, cetyl 2-ethyl hexanoate 2-ethylhexyl palmitate, glyceryl trimyristate, tri-2-heptyl undecanoic acid glyceride, methyl castor oil fatty acid, oleyl oleate, aceto glyceride, 2-heptylundecyl palmitate, diisobutyl adipate, 2-octyldodecyl N-lauroyl-L-glutamate, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, and triethyl citrate.

Examples of the silicone oils include chain polysiloxanes (for example, dimethylpolysiloxane, methylphenyl polysiloxane, and diphenyl polysiloxane); ring polysiloxanes (for example, octamethylcyclotetrasiloxane, decamethyl cyclopentasiloxane, and dodecamethyl cyclohexasiloxane), silicone resins having a three-dimensional network structure, silicone rubbers, various modified polysiloxanes (amino-modified polysiloxane, polyether-modified polysiloxane, alkyl-modified polysiloxane, and fluorine-modified polysiloxane), and acryl silicones.

Examples of the liquid fats and oils include avocado oil, tsubaki oil, turtle fatty acid, macadamia nut oil, corn oil, mink oil, olive oil, rapeseed oil, egg yolk oil, sesame oil, persic oil, wheat germ oil, sasanqua oil, castor oil, linseed oil, safflower oil, cotton seed oil, perilla oil, soybean oil, peanut oil, tea seed oil, Japanese nutmeg oil, rice bran oil, Chinese gimlet oil, Japanese gimlet oil, jojoba oil, germ oil, and triglycerides.

Examples of the solid fats and oils include cacao butter, coconut oil, horse fat, hydrogenated coconut oil, palm oil, beef tallow, mutton tallow, hydrogenated beef tallow, palm kernel oil, lard, beef bone fat, Japanese core wax nucleus oil, hydrogenated oil, neatsfoot oil, Japanese core wax, and hydrogenated castor oil.

Examples of the waxes include beeswax, candelilla wax, cotton wax, carnauba wax, bayberry wax, tree wax, whale wax, montan wax, bran wax, lanolin, kapok wax, lanolin acetate, liquid lanolin, sugar cane wax, lanolin fatty acid isopropyl ester, hexyl laurate, reduced lanolin, jojoba wax, hard lanolin, shellac wax, POE lanolin alcohol ether, POE lanolin alcohol acetate, POE cholesterol ether, lanolin fatty acid polyethylene glycol, and POE hydrogenated lanolin ethyl alcohol ether.

<Blend Ratio>

The blend ratio of the oil component is appropriately determined based on the phase diagram; it is preferably 0.1-90 wt %, more preferably 0.5-80 wt % relative to the total amount of the sunscreen composition.

<(d) Water Soluble Ultraviolet Absorbent and/or Oil Soluble Ultraviolet Absorbent>

Examples of the water soluble ultraviolet absorbent contained in the sunscreen composition of the present invention include: benzophenone-type ultraviolet absorbents such as 2,4-dihydroxybenzophenone, 2,2'-dihydroxy-4-methoxy benzophenone, 2,2'-dihydroxy-4,4'-dimethoxybenzophenone, 2,2',4,4'-tetrahydroxy benzophenone, 2-hydroxy-4-methoxy benzophenone, 2 hydroxy-4-methoxy-4'-methylbenzophenone, 2-hydroxy-4-methoxy benzophenone-5-sulfonate, 4-phenyl benzophenone, 2-ethylhexyl-4'-phenyl-benzophenone-2-carboxylate, 2-hydroxy-4-n-octoxy benzophenone, and 4-hydroxy-3-carboxy benzophenone, the benzimidazole-type ultraviolet absorbent such as phenylbenzimidazole-5-sulfonic acid and salts thereof and phenylene-bis-benzimidazole-tetrasulfonic acid and salts thereof, as well as 3-(4'-methylbenzylidene)-d,l-camphor, 3-benzylidene-d,l-camphor, urocanic acid, and urocanic acid ethyl ester.

Examples of the oil soluble ultraviolet light absorbents contained in the sunscreen composition of the present invention include: benzoic acid-type ultraviolet light absorbents such as paraminobenzoic acid (PABA), PABA monoglyceryl ester, N,N-dipropoxy PABA ethyl ester, N,N-diethoxy PABA ethyl ester, N,N-dimethyl PABA ethyl ester, and N,N-dimethyl PABA butyl ester; anthranilic acid-type ultraviolet light absorbents such as homo mentyl-N-acetyl anthranilate; salicylic acid-type ultraviolet light absorbents such as amyl salicylate, mentyl salicylate, homo mentyl salicylate, octyl salicylate, phenyl salicylate, benzyl salicylate, and p-isopropanol phenyl salicylate; cinnamic acid-type ultraviolet absorbents such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate, 2-ethylhexyl-p-methoxy cinnamate, 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, glyceryl mono-2-ethyl hexanoyl-diparamethoxy cinnamate, and 3-methyl-4-[methyl-bis(trimethylsiloxy)silyl]butyl 3,4,5-trimethoxycinnamate; 2-phenyl-5-methyl benzoxazole, 2,2'-hydroxy-5-methylphenyl benzotriazol, 2-(2'-hydroxy-5'-t-octylphenyl)benzotriazol, 2-(2'-hydroxy-5'-methylphenyl)benzotriazol, dibenzaladine, dianisoylmethane, 4-methoxy-4'-t-butyl dibenzoyl-methane, and 5-(3-dimethyl-2-norbonlylidene) 2-pentane-2-one, and octocrylene.

Furthermore, ingredient (d), particularly the water soluble ultraviolet absorbent, should preferably be one two, or more selected from phenylbenzimidazole sulfonate, 2-hydroxy-4-methoxy benzophenone-5-sulfonate, 4 (2-β-glucopyrano-siloxy)propoxy-2-hydroxybenzophenone, and bis-sodium phenylene-1,4-bis(2-benzimidazyl)-3,3'-5,5'-tetrasulfonate. The oil soluble ultraviolet absorbent contained in the sunscreen composition of the present invention should preferably be one, two, or more selected from 2-ethylhexyl-p-methoxy-cinnamate, 4-tert-butyl-4'-methoxydibenzoylmethane, octocrylene, 2,4-bis-[{4-(2-ethylhexyloxy)-2-hydroxy}-phenyl]-6-(4-methoxyphenyl)-1,3,5-triazine, methylene bis-benzotriazolyl tetramethylbutylphenol, 2,4,6-tris-[4-(2-ethylhexyloxycarbonyl)anilino]-1,3,5-triazine, diethylamino hydroxybenzoyl hexyl benzoate, oxybenzone, and 2,2'-dihydroxy-4,4'-dimethoxy benzophenone.

<Blend Ratio>

The blend ratio of the water soluble ultraviolet absorbent and/or the oil soluble ultraviolet absorbent is appropriately determined based on the phase diagram; it is preferably 0.1-20 wt %, more preferably 0.3-15 wt % relative to the total amount of the sunscreen composition.

Other ingredients commonly used in external preparations of cosmetics and quasi-drugs can be blended as necessary into the sunscreen composition of the present invention as long as the purpose/effect of the present invention is not adversely affected; examples include water soluble alcohols and thickeners; furthermore, if desired, powders such as inorganic pigments and constitutional pigments, humectants, chelating agents, preservatives, colorings, and perfumes can be blended in.

Various water soluble alcohols can be blended into the sunscreen composition of the present invention.

The water soluble alcohol is one, two, or more selected from lower alcohols, polyhydric alcohols, polyhydric alcohol polymers, dihydric alcohol alkyl ethers, dihydric alcohol ether esters, glyceryl monoalkyl ethers, sugar alcohols, monosaccharides, oligosaccharides, polysaccharides, and derivatives thereof.

Examples of the lower alcohols include ethanol, propanol, isopropanol, isobutyl alcohol, and t-butyl alcohol.

Examples of the polyhydric alcohols include: dihydric alcohols (for example, dipropylene glycol, 1,3-butylene glycol, ethylene glycol, trimethylene glycol, 1,2-butylene glycol, tetramethylene glycol, 2,3-butylene glycol, pentamethylene glycol, 2-butene-1,4-diol, hexylene glycol, and octylene glycol); trihydric alcohols (for example, glycerin and trimethylolpropane); tetrahydric alcohols (for example, diglycerin and pentaerythritol such as 1,2,6-hexanetriol); pentahydric alcohols (for example, xylitol and triglycerin); hexahydric alcohols (for example, sorbitol and mannitol); polyhydric alcohol polymers (for example, diethylene glycol, dipropylene glycol, triethylene glycol, polypropylene glycol, tetraethylene glycol, diglycerin, triglycerin, tetraglycerin, and polyglycerin); dihydric alcohol alkyl ethers (for example, ethylene glycol monomethyl ether, ethylene glycol monoethyl ether, ethylene glycol monobutyl ether, ethylene glycol monophenyl ether, ethylene glycol monohexyl ether, ethylene glycol mono 2-methyl hexyl ether, ethylene glycol isoamyl ether, ethylene glycol benzyl ether, ethylene glycol isopropyl ether, ethylene glycol dimethylether, ethylene glycol diethyl ether, and ethylene glycol dibutyl ether, diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methylethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, and dipropylene glycol butyl ether); dihydric alcohol ether esters (for example, ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, and propylene glycol monophenyl ether acetate); glyceryl mono alkyl ethers (for example, chimyl alcohol, selachyl alcohol, and batyl alcohol); sugar alcohols (for example, maltotriose, mannitol, sucrose, erythritol, glucose, fructose, starch amylolysis sugar, maltose, and alcohol prepared by the reduction of starch amylolysis sugar); glysolid; tetrahydro furfuryl alcohol; POE-tetrahydro furfuryl alcohol; POP-butyl ether; POP/POE-butyl ether; tripolyoxypropylene glyceryl ether; POP-glyceryl ether, POP-glyceryl ether phosphoric acid; POP/POE-pentane erythritol ether, and polyglycerin.

Examples of the monosaccharides include: trioses (for example, D-glyceryl aldehyde and dihydroxyacetone); tetroses (for example, D-etythrose, D-erythrulose, D-threose, and erythritol); pentoses (for example, L-arabinose, D-xylose, L-lyxose, D-arabinose, D-ribose, D-ribulose, D-xylulose, and L-xylulose); hexoses (for example, D-glucose, D-talose, D-psicose, D-galactose, D-fructose, L-galactose, L-mannose, and D-tagatose); heptoses (for example, aldoheptose and heprose); octoses (for example, octurose); deoxysugars (for example, 2-deoxy-D-ribose, 6-deoxy-L-galactose, and 6-deoxy-L-mannose); amino sugars (for example, D-glucosamine, D-galactosamine, sialic acid, amino uronic acid, and muramic acid); and uronic acid (for example, D-glucuronic acid, D-mannuronic acid, L-guluronic acid, D-galacturonic acid, and L-iduronic acid).

Examples of the oligosaccharides include sucrose, gentianose, umbelliferose, lactose, planteose, isolignoses, α,α-trehalose, raffinose, lignoses, umbilicine, stachyose and verbascose.

Examples of polysaccharides include cellulose, quince seed, starch, galactan, dermatan sulfate, glycogen, gum arabic, heparan sulfate, traganth gum, keratan sulfate, chondroitin, xanthan gum, guar gum, dextran, kerato sulfate, locust bean gum, and succinoglucan.

Examples of the polyol include polyoxyethylene methyl glucoside (Glucam E-10) and polyoxypropylene methyl glucoside (Glucam P-10).

Various thickeners can be blended into the sunscreen composition of the present invention.

Examples of the thickeners include: gum arabic, carrageenan, karaya gum, gum tragacanth, carob gum, quince seed (*Cyclonia oblonga*), casein, dextrin, gelatin, sodium pectate, sodium arginate, methyl cellulose, ethyl cellulose, CMC, hydroxy ethyl cellulose, hydroxypropyl cellulose, PVA, PVM, PVP, sodium polyacrylate, carboxy vinyl polymer, locust bean gum, guar gum, tamarind gum, cellulose dialkyl dimethylammonium sulfate, xanthan gum, aluminum magnesium silicate, bentonite, hectorite, AlMg silicate (beagum), laponite, and silicic acid anhydride.

Examples of the natural water-soluble polymer include: plant-type polymers (for example, gum arabic, gum tragacanth, galactan, guar gum, carob gum, karaya gum, carrageenan, pectin, agar, quince seed (*Cyclonia oblonga*), algae colloids (brown algae extract), starches (rice, corn, potato, and wheat), and glycyrrhizic acid); microorganism-type polymers (for example, xanthan gum, dextran, succinoglucan, and pullulan); and animal-type polymers (for example, collagen, casein, albumin, and gelatin).

Examples of the semisynthetic water-soluble polymers include: starch-type polymers (for example, carboxymethyl starch and methylhydroxypropyl starch); cellulosic polymers (for example, methyl cellulose, ethyl cellulose, methylhydroxypropyl cellulose, hydroxyethyl cellulose, cellulose sodium sulfate, hydroxypropyl cellulose, carboxymethylcellulose, sodium carboxymethyl cellulose, crystal cellulose, and cellulose powder); and alginic acid-type polymers (for example, sodium alginate and propylene glycol alginate).

Examples of the synthetic water-soluble polymers include: vinyl polymers (for example, polyvinyl alcohol, polyvinyl methyl ether, polyvinylpyrrolidone, carboxy vinyl polymer); polyoxyethylene-type polymers (for example, polyethylene glycol 20,000, 40,000, 60,000, etc.); acrylic polymers (for example, sodium polyacrylate, polyethylacrylate, and polyacrylamide); polyethyleneimine; and cationic polymers.

Examples of the powder ingredients include inorganic powders (for example, talc, kaolin, mica, sericite, muscovite, phlogopite, synthetic mica, lepidolite, biotite, vermiculite, magnesium carbonate, calcium carbonate, aluminum silicate, barium silicate, calcium silicate, magnesium silicate, strontium silicate, tungstic acid metal salt, magnesium, silica, zeolite, barium sulfate, firing calcium sulfate (calcined gypsum), calcium phosphate, fluorine-apatite, hydroxy apatite, ceramic powder, metallic soaps (for example, zinc myristate, calcium palmitate, and aluminum stearate), and boron nitride); organic powders (for example, polyamide resin powder (nylon powder), polyethylene powder, poly-methyl methacrylate powder, polystyrene powder, powders of the copolymer resin of styrene and acrylic acid, benzoguanamine resin powder, polytetrafluoroethylene powder, and cellulose powder); inorganic white pigments (for example, titanium dioxide and zinc oxide); inorganic red pigments (for example, iron oxide (red iron oxide) and iron titanate); inorganic brown pigments (for example, γ-iron oxide); inorganic yellow pigments (for example, yellow iron oxide and loess); inorganic black pigments (for example, black iron oxide and low oxides of titanium); inorganic purple pigments (for example, mango violet, cobalt violet); inorganic green pigments (for example, chromium oxide, chromium hydroxide, and cobalt titanate); inorganic blue pigments (for example, ultramarine blue and Berlin blue); pearl pigment (for example, titania coated mica, titania coated bismuth oxychloride, titania coated talc, coloration titania coated mica, bismuth oxychloride, fish scale flakes); metal powder pigments (for example, aluminium powder, copper powder); organic pigments such as Zr, barium or aluminium rake (for example, organic pigments such as red 201, red 202, red 204, red 205, red 220, red 226, red 228, red 405, orange 203, orange 204, yellow 205, yellow 401 and blue 404, as well as red 3, red 104, red 106, red 227, red 230, red 401, red 505, orange 205, yellow 4, yellow 5, yellow 202, yellow 203, green 3 and blue 1); and natural colors (for example, chlorophyll and β-carotene).

Examples of the humectant include chondroitin sulfate, hyaluronic acid, mucoitin sulfuric acid, charonic acid, atelocollagen, cholesteryl-12-hydroxy stearate, sodium lactate, bile salt, dl-pyrrolidone carboxylic acid salt, short chain soluble collagen, diglycerin (E0) P0 adduct, chestnut rose fruit extract, yarrow extract, and sweet clover extract.

Examples of the sequestering agents include 1-hydroxy ethane-1,1-diphosphonic acid, 1-hydroxy ethane-1,1-diphosphonic acid tetrasodium salt, disodium edetate, trisodium edetate, tetrasodium edetate, sodium citrate, sodium polyphosphate, sodium metaphosphate, gluconic acid, phosphoric acid, citric acid, ascorbic acid, succinic acid, and trisodium ethylene diaminehydroxyethyl triacetate.

Examples of amino acids include neutral amino acids (for example, threonine and cysteine) and basic amino acids (for example, hydroxylysine). Examples of the amino acid derivatives include sodium acyl sarcosinate (sodium N-lauroyl sarcosinate), acyl glutamate, sodium acyl β-alanine, and glutathione.

Examples of the organic amines include monoethanolamine, diethanolamine, triethanolamine, morpholine, tetrakis (2-hydroxypropyl)ethylenediamine, triisopropanolamine, 2-amino-2-methyl-1,3-propanediol, and 2-amino-2-methyl-1-propanol.

Examples of polymer emulsions include acrylic resin emulsions, ethyl polyacrylate emulsions, acryl resin liquids, polyacrylic alkyl ester emulsions, polyvinyl acetate resin emulsions, and natural rubber latex.

Examples of the pH adjustment agents include buffers such as lactic acid-sodium lactate, citric acid-sodium citrate, and succinic acid-sodium succinate.

Examples of vitamins include vitamins A, B1, B2, B6, C and E as well as their derivatives, pantothenic acid and its derivatives, and biotin.

Examples of the antioxidants include tocopherols, dibutyl hydroxytoluene, butyl hydroxyanisole, and gallic acid ester.

Examples of antioxidants aids include phosphoric acid, citric acid, ascorbic acid, maleic acid, malonic acid, succinic acid, fumaric acid, cephalin, hexametaphosphate, phytic acid, and ethylene diamine tetraacetic acid.

Examples of other possible ingredients include antiseptics (methylparaben, ethylparaben, butylparaben, and phenoxyethanol); antiphlogistic agents (for example, glycyrrhizic acid derivatives, glycyrrhetinic acid derivatives, salicylic acid derivatives, hinokitiol, zinc oxide, and allantoin); whitening agents (for example, creeping saxifrage extract and arbutin); various extracts (for example, Phellodendri Cortex, goldthread, lithospermum root, Paeonia lactiflora, Swertia japonica, Birch, sage, loquat, carrot, aloe, Malva sylvestris, Iris, grape, Coix ma-yuen, sponge gourd, lily, saffron, Cnidium officinale, sheng jiang, Hypericum erectum, Ononis, garlic, Guinea pepper, tangerine peel, dong quai, and seaweed), activators (royal jelly, photosensitive substances, and cholesterol derivatives); blood circulation promoting agents (for example, nonyl acid valenyl amide, nicotinic acid benzyl esters, nicotinic acid β-butoxy ethyl esters, capsaicin, gingeron, cantharis tincture, Ichthammol, tannic acid, α-borneol, tocopherol nicotinate, inositol hexanicotinate, cyclandelate, cinnarizine, tolazoline, acetylcholine, verapamil, cepharanthine, and γ-orizanol); anti-seborrhea agents (for example, sulfur and thiantol); and anti-inflammatory agents (for example, tranexamic acid, thiotaurine, and hypotaurine).

The sunscreen composition of the present invention contains the aforementioned ingredients (a)-(d), to which other ingredients are added as necessary within the range that does not adversely affect the effect of the present invention, and assumes a bicontinuous microemulsion phase at 25° C.

The bicontinuous microemulsion, which is a requirement in the present invention, is a thermodynamically equilibrium state, which occurs regardless of the order of addition of the ingredients. Therefore, it can be prepared by any order of addition. However, in order to achieve the equilibrium state the fastest, it is desirable to initially mix water soluble ingredients such as water, the surfactant, the water soluble ultraviolet absorbent, and salt to obtain an aqueous solution that already has a sufficiently lowered interfacial tension, and subsequently gradually add the oil soluble substances such as the oil component and the oil soluble ultraviolet absorbent as stirring is conducted.

By preparing the phase diagram as shown in FIG. 1, it is possible to determine the blend ratios of the essential ingredients (a)-(d) to prepare a sunscreen composition in the bicontinuous microemulsion phase. The apexes of the phase diagram in FIG. 1 are the A ingredient, the B ingredient, and water; the compositions of the A ingredient and the B ingredient are as follows:

<A Ingredient>

| | |
|---|---|
| Imidazolinium betaine | 35.0 |
| Sodium polyoxyethylene lauryl ether sulfate | 15.0 |
| 2-ethylhexylmonoglyceryl ether | 30.0 |
| Phenylbenzimidazolesulfonic acid | 12.5 |
| Triethanolamine | 7.5 |

<B Ingredient>

| | |
|---|---|
| Octyl octanoate | 75.0 |
| 2-ethylnexyl-p-methoxycinnamate | 25.0 |

The preparation method of the phase diagram of FIG. 1 is shown below.

1: The A ingredient, B ingredient, and water are weighed and put into a threaded-mouth test tube, shaken hard, and placed quietly in a thermostatic water bath to observe the state of the solution. If it is not turbid and completely transparent, it is in one phase. If it is turbid, it is further left still for a long period of time for each phase to separate. In rare cases where the phase separation is very slow and the deterioration of the ingredients is a concern, a centrifuge is used. In this case, it is necessary to use a type that allows temperature control.

2: If the solution is in one phase, the next step is to determine whether it is the bicontinuous microemulsion phase, the micelle aqueous solution phase, the liquid crystal phase, or the reverse micelle oil solution phase. Methods to make this determination include evaluation based on the viscosity, the optical isotropy (anisotropy), electrical conductivity measurement, polarizing microscope observation, and X-ray structure analysis.

3: When multiple phases coexist in the solution, the optical isotropy (anisotropy) is verified after complete phase separation. One of these coexisting phases is the phase of the nearby one phase region. To confirm this definitely, several solutions having gradually varying solution compositions toward the nearby one phase region are prepared; the confirmation can be made by observing that said phase in the multi-phase solution gradually occupies more volume relative to the total solution and eventually the solution becomes one phase. It is also possible to consider the specific gravity; confirmation can be made by observing the position of each phase in the test tube. The bicontinuous microemulsion phase of the present invention generally has a specific gravity lighter than that of the water phase or the micelle aqueous solution phase and heavier than that of the oil phase and the reverse micelle oil solution phase, but this depends on the constituent ingredients (system). The specific gravities of the bicontinuous microemulsion phase and the lamella liquid crystal phase are similar, but they can be distinguished from each other by the optical isotropy.

4: Following the aforementioned procedure, many solutions are prepared and the phases that appear for each composition are identified and the regions are determined to complete the phase equilibrium diagram.

A bicontinuous microemulsion phase is a solution in which a surfactant aggregates infinitely: it stands for an optically isotropic transparent low viscosity solution in which both water and oil are continuous. It is also called the middle phase microemulsion phase, bicontinuous phase, sponge phase, L3 phase, or D phase; in the present invention it gives superior ultraviolet protection and texture during use.

In terms of external appearance, the bicontinuous microemulsion is an optically isotropic transparent low viscosity one phase region. To distinguish it from other isotropic one phase regions such as the micelle aqueous solution, reverse micelle oil solution, and liquid crystal phase, the following method is effective.

Whether or not the sunscreen composition containing ingredients (a)-(d) is in a bicontinuous microemulsion phase can be determined by, for example, (1) evaluation based on the external appearance, (2) preparation of a phase equilibrium diagram, (3) electric conductivity measurement, (4) self diffusion coefficient measurement with NMR, (5) electron microscope observation of replica prepared with the freeze fracture method. Any of these methods can be used for the determination.

(1) For evaluation based on external appearance, the bicontinuous microemulsion phase is an optically isotropic transparent low viscosity one phase region. Differentiation with the liquid crystal phase, which is optically anisotropic, can be made by holding the sample between two polarized plates with 90 degree phase difference between each other and verifying that there is no light transmission. To distinguish the bicontinuous microemulsion phase from other isotropic one phase regions such as the micelle aqueous solution and reverse micelle oil solution, methods (2)-(5) are effective.

(2) For evaluation based on preparation of a phase equilibrium diagram, it can be identified using the three-ingredient system of water/oil component/surfactant (the oil component includes a builder, a co-surfactant) by characteristics such as an isotropic transparent low viscosity one phase region that is not continuous from the water or oil apex; these characteristics vary depending on the constituent system (ingredients).

(3) In terms of the electric conductivity measurement, it is known that the conductivity of the bicontinuous microemulsion phase is approximately ⅔ of that of the micelle aqueous solution obtained from the same system.

(4) The self diffusion coefficient measurement by NMR is a method described in detail in J. Colloid Interface Sci., 1981, 83, 569 by Lindman and others, for example.

(5) Electron microscopic observation of the phase sample prepared using the freeze fracture method can give an image in which both water and oil are continuous in the bicontinuous microemulsion phase. This image allows easy differentiation from the image of spherical aggregates obtained from the micelle aqueous solution wherein water or oil is continuous. This method is described in detail in Colloid polym. Sci., 1994, 272, 604 by Imae and others.

EXAMPLES

The present invention is described in detail below by referring to Examples. The present invention is not limited to these examples. The blend ratios are in wt % units.

The sunscreen cosmetic of each Test example was prepared with a conventional method and comparison was made in terms of the aggregation state (whether or not the bicontinuous microemulsion phase is observed at 25° C.) and the effectiveness as a sunscreen cosmetic.

In the following Test examples, numbers of Test examples that contain (a) surfactant, (b) water, (c) oil component, and (d) water soluble ultraviolet absorbent and/or oil soluble ultraviolet absorbent and assume the bicontinuous microemulsion phase at 25° C., and therefore are Examples of the present invention, are Test examples 1-1, 1-2, 2-1, 3-1, 4-1, 5-1 through 5-4, 6-1 through 6-4, and 7-1. Test examples other than the aforementioned do not assume the bicontinuous microemulsion phase at 25° C. and therefore are not Examples of the present invention.

The evaluation method used for each Test example is described first.

Evaluation (1): Aggregation State

The aggregation state of the sunscreen composition of the present invention was evaluated. For determination of the bicontinuous microemulsion phase, the method described in "0081" was used.

L3: The aggregation state assumes one phase which is the bicontinuous microemulsion phase.

L1: The aggregation state assumes one phase which is the micelle aqueous solution phase.

L2: The aggregation state assumes one phase which is the reverse micelle oil solution phase.

II: Water separation, oil separation, etc. is occurring.

O/W: The oil-in-water emulsion state is assumed.

W/O: The water-in-oil emulsion state is assumed.

Evaluation (2): Ultraviolet Protection Effect

The ultraviolet protection effect of the sunscreen composition of the present invention was evaluated. A prescribed amount of the sunscreen composition of each Test example was applied on a polymethyl methacrylate plate and the absorbance spectrum was measured to evaluate the ultraviolet protection effect. In the table, the absorbance of each sunscreen composition at the wavelength of 310 nm was shown. The larger the value, the superior the ultraviolet protection effect.

Evaluation (3): Good Absorption

The absorption into the skin during use was evaluated with actual use testing of each Test example by ten specialized panelists. The evaluation criteria are as follows:

⊚: Eight or more panelists recognized good absorption during use.

○: Six or more and less than eight panelists recognized good absorption during use.

Δ: Three or more and less than six panelists recognized good absorption during use.

x: Less than three panelists recognized good absorption during use.

Evaluation (4): Absence of Stickiness

The absence of stickiness during and after use was evaluated with actual use testing of each Test example by ten specialized panelists. The evaluation criteria are as follows:

⊚: Eight or more panelists recognized absence of stickiness during and after use.

○: Six or more and less than eight panelists recognized absence of stickiness during and after use.

Δ: Three or more and less than six panelists recognized absence of stickiness during and after use.

x: Less than three panelists recognized absence of stickiness during and after use.

Evaluation (5): Uniformity of the Coating Film

A sample was prepared with a fluorescent substance added to the oil phase. This was applied on a slide glass and dried for 15 minutes; the coating film was microscopically observed and the uniformity of the coating film was evaluated based on the area ratio of the oil phase (which generates white fluorescence) and the water phase.

⊚: The coating film is extremely uniform.

○: The coating film is highly uniform.

Δ: The coating film is slightly not uniform.

x: The coating film is not uniform.

<Addition of the Oil Soluble Ultraviolet Absorbent>

Sunscreen compositions of Test examples having the compositions described in the following Table 1 were prepared and the evaluation tests were conducted for the aforementioned evaluations (1)-(5).

TABLE 1

|  | Test example (%) | | | | |
| --- | --- | --- | --- | --- | --- |
|  | 1-1 | 1-2 | 1-3 | 1-4 | 1-5 |
| Imidazoliniun betaine | 9.0 | | | | |
| POE (2.5) sodium lauryl ether sulfate | 3.8 | | | | |
| 2-ethylhexyl monoglyceryl ether | 6.4 | | | | |
| POE (8) glycerin monoisostearate | | 20.8 | | | |
| POE (60) hydrogenated castor oil | | | 5 | | |
| POE(20) POP (8) cetyl ether | | | | | 3 |
| Alkyl acrylate/methacrylate copolymer | | | | 0.1 | |
| Caustic potash | | | | 0.06 | |
| Ethanol | | 8.9 | | | |
| Dipropylene glycol | | | | | 7 |
| Octyl octanoate | 15 | 15 | 15 | 15 | 15 |
| 2-ethylhexyl-p-methoxycinnamate | 5 | 5 | 5 | 5 | 5 |
| Citric acid | 0.01 | 0.01 | 0.01 | 0.01 | 0.01 |
| Sodium citrate | 0.09 | 0.09 | 0.09 | 0.09 | 0.09 |
| Chelating agent | Appropriate amount | Appropriate amount | Appropriate amount | Appropriate amount | Appropriate amount |
| Ion-exchanged water | Balance | Balance | Balance | Balance | Balance |
| Evaluation 1: Aggregation state | L3 | L3 | O/W | O/W | O/W |
| Evaluation 2: Ultraviolet protection effect | 1.47 | 1.39 | 1.01 | 0.95 | 1.15 |
| Evaluation 3: Good absorption | ◎ | ◎ | ○ | Δ | ○ |
| Evaluation 4: Absence of stickiness | ◎ | ◎ | Δ | ◎ | Δ |
| Evaluation 5: Uniformity of the coating film | ◎ | ◎ | Δ | X | ○ |

Figure 2:
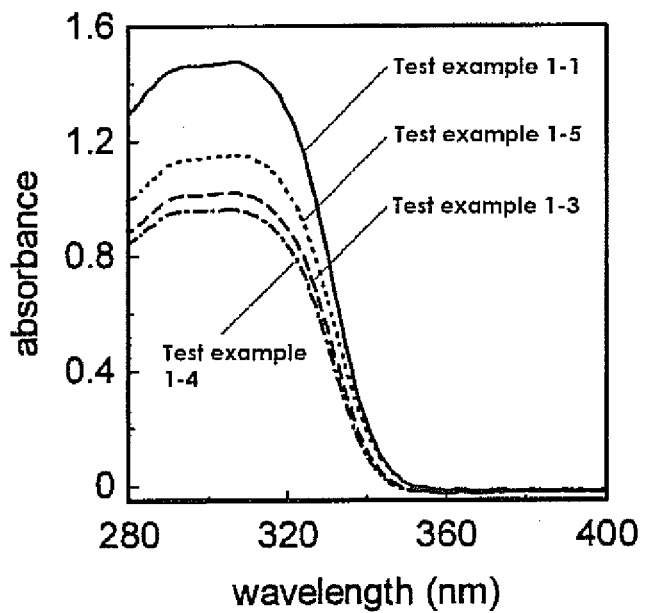
FIG. 2 is absorbance spectra of Test examples 1-1, 1-3, 1-4, and 1-5.

The absorbance spectrum measurement results of Test examples 1-1 and 1-3 through 1-5 are shown in FIG. 2.

The results in Table 1 indicate that, although Test examples 1-1 through 1-5 were all the same in terms of the concentrations of the oil component (octyl octanoate) and the ultraviolet absorbent (2-ethylhexyl-p-methoxycinnamate), Test examples 1-3 through 1-5, which assumed the O/W emulsion state, were all inferior in terms of the ultraviolet protection effect and also somewhat inferior in terms of the texture during use. Test example 1-4 also was somewhat inferior in terms of the uniformity of the coating film.

On the other hand, Test example 1-1, which contained an ionic surfactant for ingredient (a), and Test example 1-2, which contained a nonionic surfactant for ingredient (a), both formed the bicontinuous microemulsion phase and were superior in all the evaluations (1)-(5).

<Addition of the Water Soluble Ultraviolet Absorbent>

Sunscreen compositions of Test examples having the compositions described in the following Table 2 were prepared and the evaluation tests were conducted for the evaluations (1)-(5).

TABLE 2

|  | Test example (%) | | | | |
| --- | --- | --- | --- | --- | --- |
|  | 2-1 | 2-2 | 2-3 | 2-4 | 2-5 |
| Imidazoliniun betaine | 8.4 | 1.1 | | | |
| POE (3) sodium lauryl ether sulfate | 3.6 | 0.5 | | | |
| 2-ethylhexyl monoglyceryl ether | 7.14 | | | | |
| POE (60) hydrogenated castor oil | | | 5 | | |
| POE (20) POP (8) cetyl ether | | | | | 3 |
| Alkyl acrylate/methacrylate copolymer | | | | 0.1 | |
| Caustic potash | | | | 0.06 | |
| Phenylbenzimidazolesulfonic acid | 3.0 | 3.0 | 3.0 | 3.0 | 3.0 |
| Triethanolamine | 1.78 | 1.78 | 1.78 | 1.78 | 1.78 |
| Dipropylene glycol | | | | | 7 |
| Octyl octanoate | 20 | | 20 | 20 | 20 |
| Citric acid | 0.01 | 0.01 | 0.01 | 0.01 | 0.01 |
| Sodiun citrate | 0.09 | 0.09 | 0.09 | 0.09 | 0.09 |
| Chelating agent | Appropriate amount | Appropriate amount | Appropriate amount | Appropriate amount | Appropriate amount |
| Ion-exchanged water | Balance | Balance | Balance | Balance | Balance |
| Evaluation 1: Aggregation state | L3 | L1 | O/W | O/W | O/W |
| Evaluation 2: Ultraviolet protection effect | 0.77 | 0.37 | 0.41 | 0.25 | 0.54 |
| Evaluation 3: Good absorption | ◎ | X | ○ | Δ | ○ |
| Evaluation 4: Absence of stickiness | ◎ | ◎ | Δ | ◎ | Δ |
| Evaluation 5: Uniformity of the coating film | ◎ | X | Δ | X | ○ |

The results in Table 2 indicate that, although Test examples 2-2 through 2-5 are all the same in terms of the concentrations of the ultraviolet absorbent (phenylbenzimidazole sulfonic acid), Test example 2-2, which assumed the micelle aqueous solution phase, and Test examples 2-3 through 2-5, which assumed the O/W emulsion state, are all inferior in terms of the ultraviolet protection effect and also somewhat inferior in terms of the tactile sensation during use. Test examples 2-2 and 2-4 also were somewhat inferior in terms of the uniformity of the coating film.

Whereas, Test example 2-1 formed the bicontinuous microemulsion phase and were superior in all the evaluations (1)-(5).

<Addition of the Surfactant>

Sunscreen compositions of Test examples having the compositions described in the following Table 3 were prepared and the evaluation tests were conducted for the evaluations (1)-(5).

TABLE 3

|  | Test example (%) | |
| --- | --- | --- |
|  | 3-1 | 3-2 |
| Cocoyl amidepropylbetaine | 8.4 |  |
| POE (3) sodium palmityl ether sulfate | 3.6 |  |
| 2-ethylhexyl monoglyceryl ether | 7.14 |  |
| Phenylbenzimidazolesulfonic acid | 3.0 | 3.0 |
| Triethanolamine | 1.78 | 1.78 |
| Isononyl isononanoate | 15 | 15 |
| 2-ethylhexyl-p-methoxycinnamate | 5 | 5 |
| Citric acid | 0.01 | 0.01 |
| Sodium citrate | 0.09 | 0.09 |
| Chelating agent | Appropriate amount | Appropriate amount |
| Ion-exchanged water | Balance | Balance |
| Evaluation 1: Aggregation state | L3 | II |
| Evaluation 2: Ultraviolet protection effect | 1.66 | — |
| Evaluation 3: Good absorption | ◉ | — |
| Evaluation 4: Absence of stickiness | ◉ | — |
| Evaluation 5: Uniformity of the coating film | ◉ | — |

The results of Table 3 indicate that Test example 3-2, which did not contain a surfactant, could not assume the solubilized state or the emulsified state and assumed a separated state, which rendered evaluation impossible.

Whereas, Test example 3-1, which contained a surfactant, formed the bicontinuous microemulsion phase and was superior in all the evaluations (1)-(5).

<The Effect of the Bicontinuous Microemulsion Phase>

Sunscreen compositions of Test examples having the compositions described in the following Table 4 were prepared and the evaluation tests were conducted for the evaluations (1)-(5).

TABLE 4

|  | Test example (%) | | |
| --- | --- | --- | --- |
|  | 4-1 | 4-2 | 4-3 |
| Imidazolinium betaine | 6.7 | 2.0 | 6.7 |
| POE (2) sodium lauryl ether sulfate | 2.9 | 0.9 | 2.9 |
| 2-ethylhexyl monoglyceryl ether | 5.7 | 1.7 |  |
| Phenylbenzimidazolesulfonic acid | 2.4 | 2.4 | 2.4 |
| Triethanolamine | 1.4 | 1.4 | 1.4 |
| Octyl octanoate | 15 | 15 | 15 |
| 2-ethylhexyl-p-methoxycinnamate | 5 | 5 | 5 |
| Citric acid | 0.01 | 0.01 | 0.01 |
| Sodium citrate | 0.09 | 0.09 | 0.09 |
| Chelating agent | Appropriate amount | Appropriate amount | Appropriate amount |
| Ion-exchanged water | Balance | Balance | Balance |
| Evaluation 1: Aggregation state | L3 | O/W | O/W |
| Evaluation 2: Ultraviolet protection effect | 1.65 | 1.22 | 1.46 |
| Evaluation 3: Good absorption | ◉ | Δ | Δ |
| Evaluation 4: Absence of stickiness | ◉ | X | Δ |
| Evaluation 5: Uniformity of the coating film | ◉ | Δ | ○ |

Figure 3:
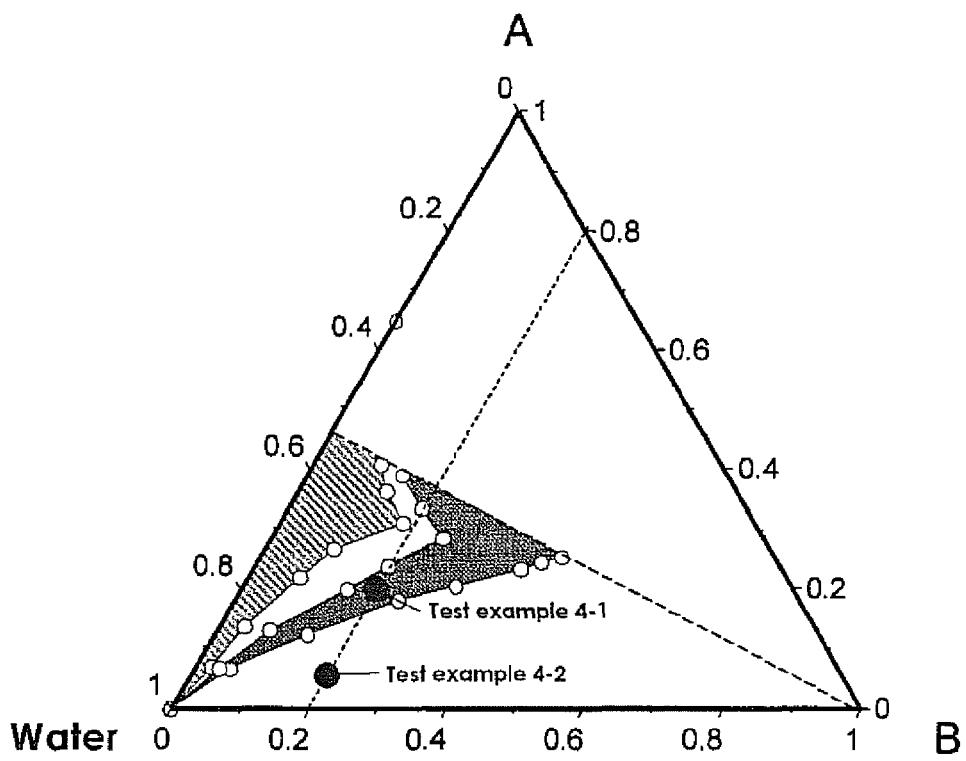
FIG. 3 is a phase diagram showing the compositions of Test examples 4-1 and 4-2 on FIG. 1.

The compositions of Test examples 4-1 and 4-2 in the phase diagram in FIG. 1 are shown in FIG. 3. It is shown that Test examples 4-1 and 4-2 have an identical concentration of the B ingredient (the oil component and the oil soluble ultraviolet absorbent) but Test example 4-1 forms the bicontinuous microemulsion phase and Test example 4-2 becomes multiphased. The composition of Test example 4-2 in FIG. 3 has the concentration of the water soluble ultraviolet absorbent less than that in 4-1, so a correction is made subsequently by adding the difference.

The results in Table 4 indicate that Test example 4-2, which did not form the bicontinuous microemulsion phase and assumed the O/W emulsified state, was inferior in terms of the ultraviolet protection effect and also inferior in terms of the tactile sensation during use. Test example 4-3, which did not contain 2-ethylhexylmonoglyceryl ether, a builder, similarly did not form the bicontinuous microemulsion phase and assumed the O/W emulsified state, manifesting an inferior ultraviolet protection effect and a somewhat inferior tactile sensation during use.

Whereas, Test example 4-1, which formed the bicontinuous microemulsion, was superior in all the evaluations (1)-(5).

Sunscreen compositions of Test examples having the compositions described in the following Table 5 were prepared and the evaluation tests were conducted for the evaluations (1)-(5).

TABLE 5

|  | Test example (%) | | | |
| --- | --- | --- | --- | --- |
|  | 5-1 | 5-2 | 5-3 | 5-4 |
| Imidazolinium betaine | 8.6 | 6.7 | 4.5 | 2.4 |
| POE (2) sodium lauryl sulfate | 3.7 | 2.9 | 1.9 | 1.0 |
| 2-ethylhexyl monoglyceryl ether | 7.3 | 5.7 | 3.9 | 2.1 |
| Phenylbenzimidazolesulfonic acid | 3.1 | 2.4 | 1.6 | 0.9 |
| Triethanolamine | 1.8 | 1.4 | 1 | 0.5 |
| Octyl octanoate | 22.5 | 15 | 7.5 | 3 |
| 2-ethylhexyl-p-methoxycinnamate | 7.5 | 5 | 2.5 | 1 |
| Citric acid | 0.01 | 0.01 | 0.01 | 0.01 |
| Sodium citrate | 0.09 | 0.09 | 0.09 | 0.09 |
| Chelating agent | Appropriate amount | Appropriate amount | Appropriate amount | Appropriate amount |
| Ion-exchanged water | Balance | Balance | Balance | Balance |
| Evaluation 1: Aggregation state | L3 | L3 | L3 | L3 |
| Evaluation 2: Ultraviolet protection effect | 2.02 | 1.65 | 1.10 | 0.60 |
| Evaluation 3: Good absorption | ○ | ◉ | ◉ | ○ |
| Evaluation 4: Absence of stickiness | ○ | ◉ | ◉ | ◉ |
| Evaluation 5: Uniformity of the coating film | ◉ | ◉ | ◉ | ◉ |

Figure 4:
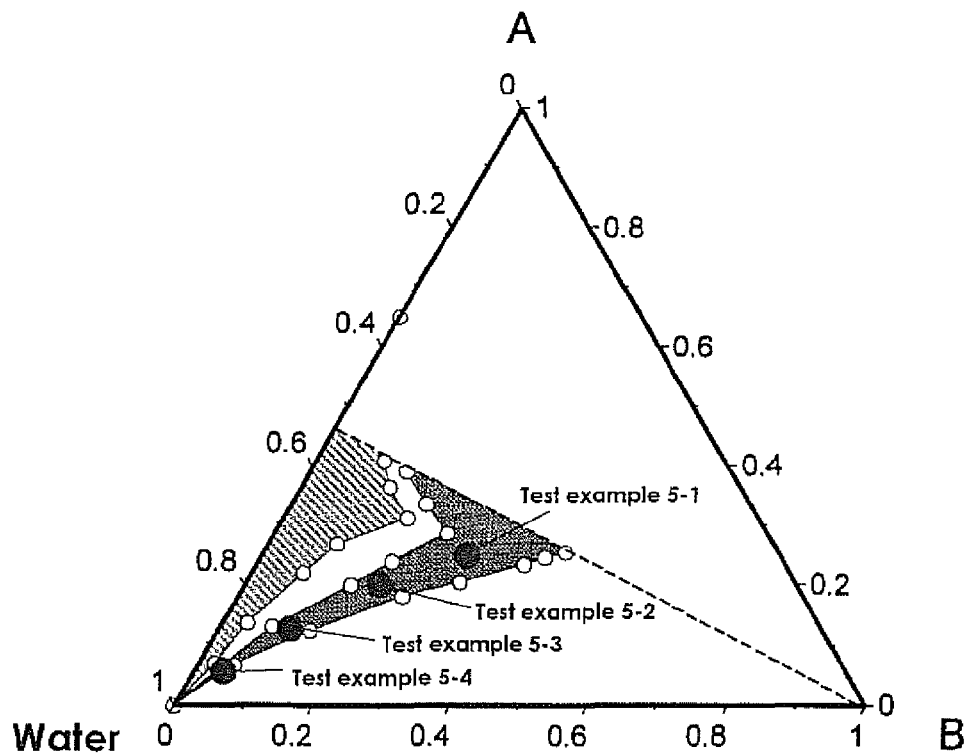
FIG. 4 is a phase diagram showing the compositions of Test examples 5-1 through 5-4 on FIG. 1.

The compositions of Test examples 5-1 through 5-4 in the phase diagram in FIG. 1 are shown in FIG. 4.

The results in Table 5 indicate that Test examples 5-1 through 5-4 formed the bicontinuous microemulsion phase, manifested a high ultraviolet protection effect in relation to the blend ratio of the ultraviolet absorbent (phenylbenzimidazole sulfonic acid and 2-ethylhexyl-p-methoxycinnamate), and all were superior in terms of the tactile sensation during use and the uniformity of the coating film.

By utilizing bicontinuous microemulsion phases having various compositions that are generated on the phase diagram of the ionic surfactant system, sunscreen compositions containing various concentrations of surfactants, oil components, and ultraviolet absorbents can be obtained.

Sunscreen compositions of Test examples having the compositions described in the following Table 6 were prepared and the evaluation tests were conducted for the evaluations (1)-(5).

Figure 5:
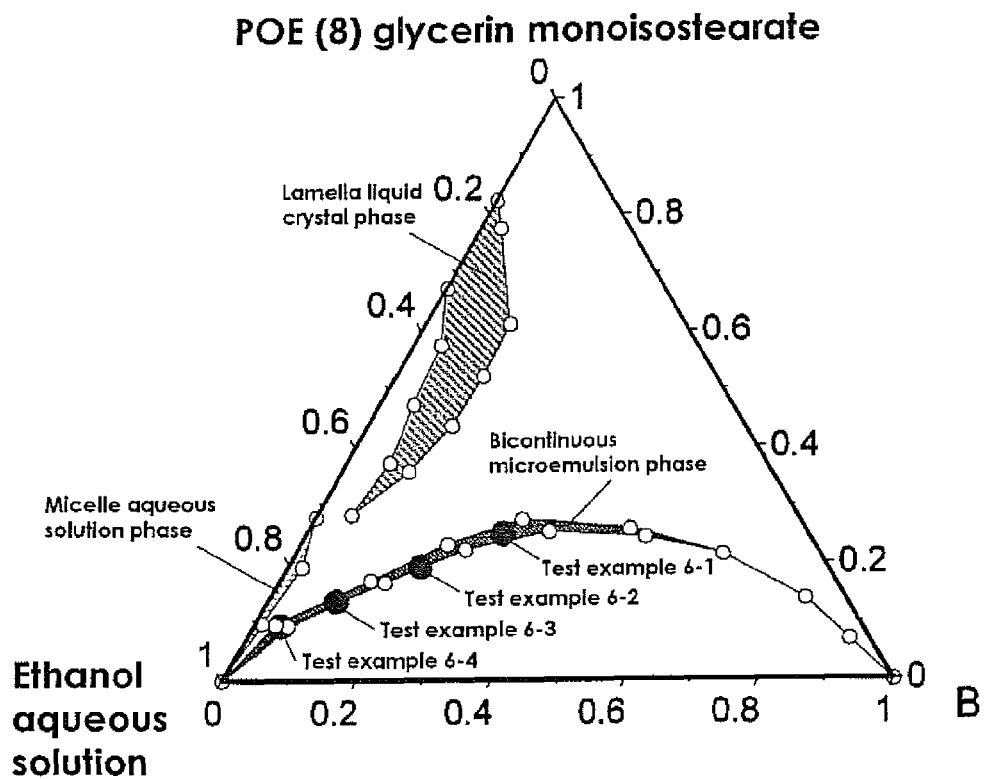
FIG. 5 is a phase diagram for determining the blend ratios of the essential ingredients (a)-(d) to prepare a sunscreen composition in the bicontinuous microemulsion phase; it is a phase diagram showing the compositions of Test examples 6-1 through 6-4.

Phase diagrams of the nonionic surfactant systems prepared to conduct this test along with the compositions of Test examples 6-1 through 6-4 are shown in FIG. 5. The apexes in the phase diagrams in FIG. 5 are POE (8) glycerin monoisostearate (HLB=10, from Nihon Emulsion Co., Ltd., product name: EMALEX GUS-108), the B ingredient, and water; the composition of the B ingredient is shown below.
<B Ingredient>

| | |
|---|---|
| Octyl octanoate | 75.0 |
| 2-ethylnexyl-p-methoxycinnamate | 25.0 |

TABLE 6

| | Test example (%) | | | |
|---|---|---|---|---|
| | 6-1 | 6-2 | 6-3 | 6-4 |
| POE (8) glycerin monoisostearate | 24.5 | 20 | 13.5 | 9.6 |
| Octyl octanoate | 22.5 | 15 | 7.5 | 3 |
| 2-ethylhexyl-p-methoxycinnamate | 7.5 | 5 | 2.5 | 1 |
| Citric acid | 0.01 | 0.01 | 0.01 | 0.01 |
| Sodium citrate | 0.09 | 0.09 | 0.09 | 0.09 |
| Chelating agent | Appropriate amount | Appropriate amount | Appropriate amount | Appropriate amount |
| Ethanol | 6.8 | 9.0 | 11.5 | 13.0 |
| Ion-exchanged water | Balance | Balance | Balance | Balance |
| Evaluation 1: Aggregation state | L3 | L3 | L3 | L3 |
| Evaluation 2: Ultraviolet protection effect | 1.65 | 1.42 | 0.93 | 0.45 |
| Evaluation 3: Good absorption | ⊚ | ⊚ | ⊚ | ○ |
| Evaluation 4: Absence of stickiness | ⊚ | ⊚ | ⊚ | ⊚ |
| Evaluation 5: Uniformity of the coating film | ⊚ | ⊚ | ⊚ | ⊚ |

The results in Table 6 indicates that Test examples 6-1 through 6-4 formed the bicontinuous microemulsion phase, manifested a high ultraviolet protection effect in relation to the blend ratio of the ultraviolet absorbent (2-ethylhexyl-p-methoxycinnamate), and all were superior in terms of the tactile sensation during use and the uniformity of the coating film.

By utilizing bicontinuous microemulsion phases having various compositions that are generated on the phase diagram of the nonionic surfactant system, sunscreen compositions containing various concentrations of surfactants, oil components, and ultraviolet absorbents can be obtained.

<The Effect of the Bicontinuous Microemulsion Phase>

Sunscreen compositions of Test examples having the compositions described in the following Table 7 were prepared and the evaluation tests were conducted for the evaluations (1)-(5).

TABLE 7

| | Test example (%) | | |
|---|---|---|---|
| | 7-1 | 7-2 | 7-3 |
| POE (8) glycerin monoisostearate | 24.5 | 7.0 | 42.0 |
| Octyl octanoate | 22.5 | 22.5 | 22.5 |
| 2-ethylhexyl-p-methoxycinnamate | 7.5 | 7.5 | 7.5 |
| Citric acid | 0.01 | 0.01 | 0.01 |
| Sodium citrate | 0.09 | 0.09 | 0.09 |
| Chelating agent | Appropriate amount | Appropriate amount | Appropriate amount |
| Ethanol | 6.8 | 9.45 | 4.2 |
| Ion-exchanged water | Balance | Balance | Balance |

TABLE 7-continued

| | Test example (%) | | |
|---|---|---|---|
| | 7-1 | 7-2 | 7-3 |
| Evaluation 1: Aggregation state | L3 | O/W | II (L3 + liquid crystal) |
| Evaluation 2: Ultraviolet protection effect | 1.65 | 1.55 | 1.58 |
| Evaluation 3: Good absorption | ⊚ | Δ | ○ |
| Evaluation 4: Absence of stickiness | ⊚ | ○ | X |
| Evaluation 5: Uniformity of the coating film | ⊚ | Δ | ○ |

Figure 6:
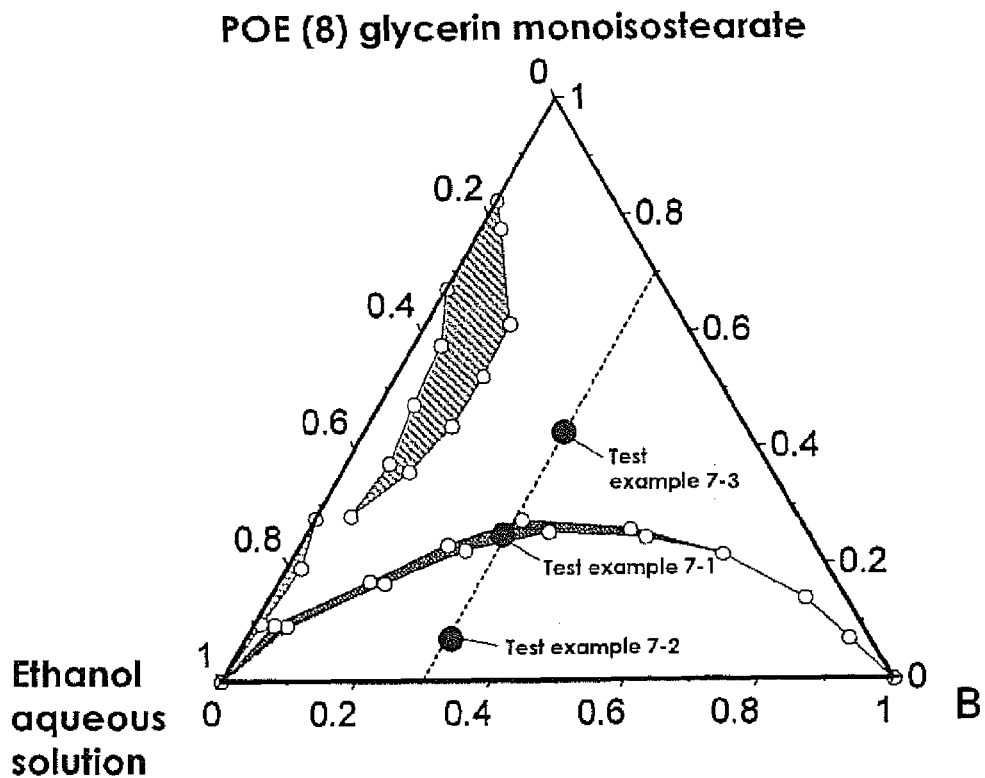
FIG. 6 is a phase diagram showing the compositions of Test examples 7-1 through 7-4 on FIG. 5.

The compositions of Test examples 7-1 through 7-3 in the phase diagram in FIG. 5 are shown in FIG. 6. It is shown that Test examples 7-1 through 7-3 have an identical concentration of the oil component and the oil soluble ultraviolet absorbent but Test example 7-1 forms the bicontinuous microemulsion phase and Test example 7-2 and 7-3 become multi-phased.

The results in Table 7 indicate that Test example 7-2, which did not form the bicontinuous microemulsion phase and assumed the O/W emulsified state, was inferior in terms of the ultraviolet protection effect and also inferior in terms of the tactile sensation during use. Test example 7-3, which assumed a multi-phase state including the bicontinuous microemulsion phase, manifested a somewhat inferior ultraviolet protection effect and an inferior tactile sensation during use.

Whereas, Test example 7-1, which formed the bicontinuous microemulsion, was superior in all the evaluations (1)-(5).

Figure 7:
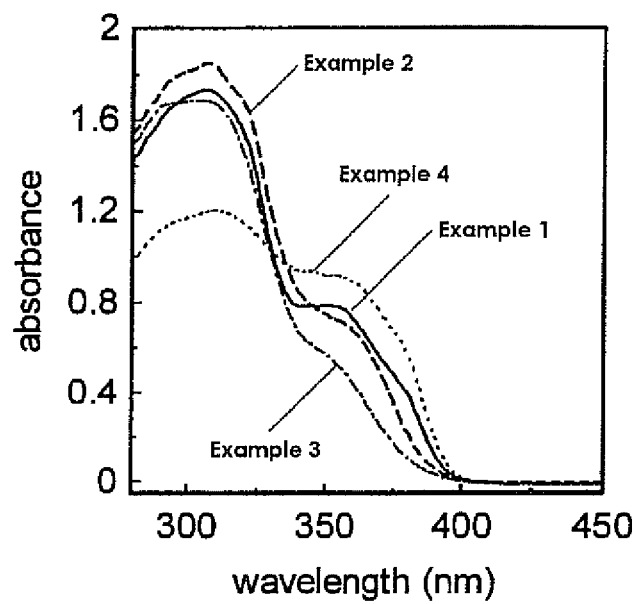
FIG. 7 is absorbance spectra of Examples 1-4.

The following are formulation examples of the sunscreen composition composed of the bicontinuous microemulsion phase of the present invention. The obtained sunscreen composition assumed the bicontinuous microemulsion phase at 25° C., manifested good safety features and a good tactile sensation during use, and exhibited a high base agent stability. The absorbance spectrum measurement results of Examples 1 through 3 are shown in FIG. 7.

Example 1

Sunscreen Lotion

| | |
|---|---|
| Imidazolinium betaine | 7.0 |
| POE (2.5) sodium lauryl sulfate | 3.0 |
| 2-ethylhexylmonoglyceryl ether | 6.0 |
| Phenylbenzimidazole sulfonic acid | 2.5 |
| Triethanolamine | 1.5 |
| Citric acid | 0.01 |
| Sodium citrate | 0.09 |
| Chelating agent | Appropriate amount |
| Ion-exchanged water | Balance |
| Octyl octanoate | 11.3 |
| 2-ethylhexyl-p-methoxycinnamate | 3.8 |
| Hexyl diethylaminohydroxybenzoylbenzoate | 0.5 |
| 2,4,6-tris[4-(2-ethylhexyloxycarbonyl)anilino]-1,3,5-triazine | 0.5 |
| 4-tert-4'-methoxybenzoylmethane | 0.5 |

Example 2

Sunscreen Mist

| | |
|---|---|
| Imidazolinium betaine | 7.0 |
| POE (2) sodium lauryl sulfate | 1.5 |
| POE (3) sodium lauryl sulfate | 1.5 |
| 2-ethylhexylmonoglyceryl ether | 5.9 |
| Phenylbenzimidazole sulfonic acid | 2.5 |
| Triethanolamine | 1.5 |
| Citric acid | 0.01 |
| Sodium citrate | 0.09 |
| Chelating agent | Appropriate amount |
| Ion-exchanged water | Balance |
| Nonyl nonanoate | 11.3 |
| 2-ethylnexyl-p-methoxycinnamate | 3.75 |
| 2,4-bis[{4-(2-ethylhexyloxy)-2-hydroxy}-phenyl]-6-(4-methoxyphenyl)-1,3,5-triazine | 1.0 |
| Octocrylene | 1.0 |

Example 3

Sunscreen Lotion

| | |
|---|---|
| Phytantriol | 28.5 |
| Citric acid | 0.01 |
| Sodium citrate | 0.09 |
| Chelating agent | Appropriate amount |
| Ion-exchanged water | Balance |
| Dimethylpolysiloxane | 61.0 |
| 2-ethylnexyl-p-methoxycinnamate | 5.0 |
| Diethylamino hydroxybenzoyl hexyl benzoate | 0.5 |

Example 4

Sunscreen Liquid

| | |
|---|---|
| Glyceryl monoisostearate | 44.4 |
| Citric acid | 0.01 |
| Sodium citrate | 0.09 |
| Chelating agent | Appropriate amount |
| Ion-exchanged water | Balance |
| Isododecane | 45.0 |
| Octocrylene | 2.2 |
| 4-tert-4'-methoxybenzoylmethane | 1.1 |
| 2,4-bis[{4-(2-ethylhexyloxy)-2-hydroxy}-phenyl]-6-(4-methoxyphenyl)-1,3,5-triazine | 0.5 |
| 2-ethylnexyl-p-methoxycinnamate | 1.6 |
| Diethylamino hydroxybenzoyl hexyl benzoate | 0.5 |

INDUSTRIAL APPLICABILITY

The present invention provides a sunscreen composition that utilizes a transparent bicontinuous microemulsion phase.

The sunscreen composition of the present invention, by utilizing the bicontinuous microemulsion phase, is used effectively as a sunscreen composition that manifests excellent ultraviolet protection ability and superior stability, spreads well on the skin when applied, exhibits superior coating film uniformity and superior absorption into the skin. Furthermore, the sunscreen composition of the present invention exhibits a superior ultraviolet protection ability and therefore it can be used effectively for various industrial products.

The invention claimed is:

1. A sunscreen composition comprising:
   (a) 0.3-30 weight percent of said sunscreen composition of a surfactant, said surfactant selected from the group consisting of:
      (i) a combination of a nonionic surfactant and an ionic surfactant,
      (ii) a nonionic surfactant,
      (iii) a combination of an anionic surfactant and an ampholytic surfactant, and
      (iv) a combination of an nonionic surfactant and an ampholytic surfactant;
   (b) 0.10-95 weight percent of said sunscreen composition of water;
   (c) 0.5-80 weight percent of said sunscreen composition of an oil component; and
   (d) 0.3-15 weight percent of said sunscreen composition of a water soluble ultraviolet absorbent and/or an oil soluble ultraviolet absorbent;
   wherein said (a) to (d) interact and are in a bicontinuous microemutsion phase at 25° C.; and wherein
   said surfactant is one or more selected from the group consisting of imidazolium betaine, POE (2.5) sodium lauryl ether sulfate, POE (8) glyceryl monostearate, POE (3) sodium lauryl ether sulfate, cocamidopropyl betaine, POE (3) sodium palmityl ether sulfate, POE (2) sodium lauryl ether sulfate, POE (3) sodium lauryl ether sulfate, phytantriol, and glyceryl monostearate;
   said oil component is either octyl octanoate, nonyl nonanoate, dimethylpolysiloxane, or isododecane;
   said water soluble ultraviolet absorbent is one or more selected from the group consisting of phenylbenzimidazole sulfonate, 2-hydroxy-4-methoxy benzophenone-5-sulfonate, 4-(2-beta-glucopyrano-siloxy)propoxy-2-hydroxybenzophenone, and bis-sodium phenylene-1,4-bis(2-benzimidazyl)-3,3'-5,5'-tetrasulfonate; and
   said oil soluble ultraviolet absorbent is one or more selected from the group consisting of 2-ethylhexyl-p-methoxycinnamate, 4-tert-4'-methoxydibenzoyl-methane, octocrylene, 2,4-bis-[{4-(2-ethythexyloxy)-2-hydroxy}-phenyl]-6-(4-methoxyphenyl)-1,3,5-triazine, methylene bis-benzotriazolyl tetrarnethyl butylphenol, 2,4,6-tris-[4-(2-ethylhexyloxycarbonyl)anilino]-1,3,5-triazine, diethylamino hydroxybenzoyl hexyl benzoate, oxybenzone, and dihydroxy dimethoxy benzophenone.

2. The sunscreen composition of claim 1, wherein said surfactant is a nonionic surfactant whose HLB is between 5 and 14.

3. The sunscreen composition of claim 1, wherein said surfactant is POE (8) glyceryl monostearate, said oil component is octyl octanoate, and said ultraviolet absorbent is 2-ethylhexyl-p-methoxycinnamate.

4. The sunscreen composition of claim 3, comprising:
   (a) 0.3-30 weight percent of said sunscreen composition of POE (8) glyceryl monostearate;
   (b) 0.1-95 weight percent of said sunscreen composition of water;
   (c) 0.5-80 weight percent of said sunscreen composition of octyl octanoate; and
   (d) 0.3-15 weight percent of said sunscreen composition of 2-ethylhexyl-p-methoxycinnamate.

* * * * *